US009050585B2

(12) United States Patent
Zhou et al.

(10) Patent No.: US 9,050,585 B2
(45) Date of Patent: Jun. 9, 2015

(54) CHEMISORPTION OF ETHYL ACETATE DURING HYDROGENATION OF ACETIC ACID TO ETHANOL

(75) Inventors: Zhenhua Zhou, Houston, TX (US); Heiko Weiner, Pasadena, TX (US); Dheeraj Kumar, Pearland, TX (US); Xiaoyan Tu, Houston, TX (US); Victor J. Johnston, Houston, TX (US); Radmila Jevtic, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 336 days.

(21) Appl. No.: 13/371,064

(22) Filed: Feb. 10, 2012

(65) Prior Publication Data

US 2013/0211150 A1    Aug. 15, 2013

(51) Int. Cl.
| C07C 27/04 | (2006.01) |
| B01J 23/89 | (2006.01) |
| C07C 29/149 | (2006.01) |
| C07C 67/56 | (2006.01) |
| C07C 31/08 | (2006.01) |
| B01J 37/02 | (2006.01) |
| B01J 37/00 | (2006.01) |

(52) U.S. Cl.
CPC .......... B01J 23/8993 (2013.01); B01J 23/8966 (2013.01); C07C 29/149 (2013.01); C07C 67/56 (2013.01); B01J 37/0205 (2013.01); B01J 23/898 (2013.01); B01J 37/0018 (2013.01); B01J 37/0201 (2013.01); C07C 31/08 (2013.01)

(58) Field of Classification Search
CPC ...................................... C07C 27/04
USPC ....................................... 568/885
See application file for complete search history.

(56) References Cited

U.S. PATENT DOCUMENTS

| 2,549,416 A | 4/1951 | Brooks |
| 2,607,807 A | 8/1952 | Ford |
| 2,882,244 A | 4/1959 | Milton |
| 3,130,007 A | 4/1964 | Breck |
| 3,361,769 A | 1/1968 | Halpern et al. |
| 3,478,112 A | 11/1969 | Karl et al. |
| 3,661,769 A | 5/1972 | Venuto et al. |
| 3,864,284 A | 2/1975 | Clippinger et al. |
| 3,953,524 A | 4/1976 | Steiner |
| 3,981,923 A | 9/1976 | Stouthamer et al. |
| 3,990,952 A | 11/1976 | Katzen et al. |
| 4,199,438 A | 4/1980 | Antos |
| 4,317,918 A | 3/1982 | Takano et al. |
| 4,337,351 A | 6/1982 | Larkins, Jr. |
| 4,374,265 A | 2/1983 | Larkins, Jr. |
| 4,395,576 A | 7/1983 | Kwantes et al. |
| 4,398,039 A | 8/1983 | Pesa et al. |
| 4,421,939 A | 12/1983 | Kiff et al. |
| 4,426,541 A | 1/1984 | King |
| 4,443,639 A | 4/1984 | Pesa et al. |
| 4,454,358 A | 6/1984 | Kummer et al. |
| 4,456,775 A | 6/1984 | Travers et al. |
| 4,476,326 A | 10/1984 | Lin et al. |
| 4,480,115 A | 10/1984 | McGinnis |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |
| 4,550,185 A | 10/1985 | Mabry et al. |
| 4,628,130 A | 12/1986 | Boumonville et al. |
| 4,678,543 A | 7/1987 | Houben et al. |
| 4,692,218 A | 9/1987 | Houben et al. |
| 4,760,171 A | 7/1988 | Isogai et al. |
| 4,777,303 A | 10/1988 | Kitson et al. |
| 4,804,791 A | 2/1989 | Kitson et al. |
| 4,826,795 A | 5/1989 | Kitson et al. |
| 4,837,368 A | 6/1989 | Gustafson et al. |
| 4,880,937 A | 11/1989 | Matsushita et al. |
| 4,985,572 A | 1/1991 | Kitson et al. |
| 4,990,655 A | 2/1991 | Kitson et al. |

(Continued)

FOREIGN PATENT DOCUMENTS

| CN | 1230458 | 10/1999 |
| CN | 102229520 | 11/2001 |

(Continued)

OTHER PUBLICATIONS

International Search Report and Written Opinion mailed Mar. 14, 2013 in corresponding International Application No. PCT/US2012/066644.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

Pestman et al., Reactions of Carboxylic Acids on Oxides, Journal of Catalysis 168:255-264 (1997).

(Continued)

Primary Examiner — Yong Chu
Assistant Examiner — Sonya Wright

(57) ABSTRACT

A hydrogenation catalyst and process using the catalyst for converting a mixture comprising acetic acid and ethyl acetate to ethanol at a first temperature, and the catalyst desorbs ethyl acetate, in the absence of hydrogen, at a second temperature that is greater than the first temperature. The catalyst has a suitable chemisorption of ethyl acetate at the first temperature in the absence of hydrogen. In one embodiment, the first temperature ranges from 125° C. to 350° C. and the second temperature ranges from 300° C. to 600° C. The catalyst comprises one or more active metals or oxide thereof on a support that comprises tungsten or an oxide thereof. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum.

7 Claims, 2 Drawing Sheets

(56) References Cited

U.S. PATENT DOCUMENTS

| | | |
|---|---|---|
| 5,008,235 A | 4/1991 | Wegman et al. |
| 5,026,908 A | 6/1991 | Smith et al. |
| 5,061,671 A | 10/1991 | Kitson et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,185,476 A | 2/1993 | Gustafson |
| 5,185,481 A | 2/1993 | Muto et al. |
| 5,198,592 A | 3/1993 | Van Beijnum et al. |
| 5,243,095 A | 9/1993 | Roberts et al. |
| 5,250,271 A | 10/1993 | Horizoe et al. |
| 5,292,704 A | 3/1994 | Lester |
| 5,292,916 A | 3/1994 | Matsuzaki et al. |
| 5,334,769 A | 8/1994 | Ferrero et al. |
| 5,350,504 A | 9/1994 | Dessau |
| 5,391,291 A | 2/1995 | Winquist et al. |
| 5,414,161 A | 5/1995 | Uhm et al. |
| 5,426,246 A | 6/1995 | Nagahara et al. |
| 5,476,827 A | 12/1995 | Ferrero et al. |
| RE35,377 E | 11/1996 | Steinberg et al. |
| 5,585,523 A | 12/1996 | Weiguny et al. |
| 5,599,976 A | 2/1997 | Scates et al. |
| 5,719,097 A | 2/1998 | Chang et al. |
| 5,767,307 A | 6/1998 | Ramprasad et al. |
| 5,821,111 A | 10/1998 | Gaddy et al. |
| 5,849,657 A | 12/1998 | Rotgerink et al. |
| 5,942,460 A | 8/1999 | Garland et al. |
| 5,945,570 A | 8/1999 | Arhancet et al. |
| 5,955,397 A | 9/1999 | Didillon et al. |
| 5,977,010 A | 11/1999 | Roberts et al. |
| 6,046,127 A | 4/2000 | Mimoun |
| 6,049,008 A | 4/2000 | Roberts et al. |
| 6,121,498 A | 9/2000 | Tustin et al. |
| 6,204,417 B1 | 3/2001 | Fisher et al. |
| 6,232,352 B1 | 5/2001 | Vidalin et al. |
| 6,281,160 B1 | 8/2001 | Basset et al. |
| 6,294,703 B1 | 9/2001 | Hara et al. |
| 6,462,231 B1 | 10/2002 | Yanagawa et al. |
| 6,462,244 B1 | 10/2002 | Huang et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,559,333 B1 | 5/2003 | Brunelle et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,074,603 B2 | 7/2006 | Verser et al. |
| 7,084,312 B1 | 8/2006 | Huber et al. |
| 7,208,624 B2 | 4/2007 | Scates et al. |
| 7,335,800 B2 | 2/2008 | Komplin et al. |
| 7,375,049 B2 | 5/2008 | Hayes et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,790,938 B2 | 9/2010 | Kawasaki et al. |
| 7,842,844 B2 | 11/2010 | Atkins |
| 7,847,134 B2 | 12/2010 | Lee et al. |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 7,964,379 B2 | 6/2011 | Verser et al. |
| 8,071,389 B2 | 12/2011 | Weck et al. |
| 8,071,821 B2 | 12/2011 | Johnston et al. |
| 8,309,782 B2 | 11/2012 | Le Peltier et al. |
| 2003/0077771 A1 | 4/2003 | Verser et al. |
| 2003/0104587 A1 | 6/2003 | Verser et al. |
| 2003/0105171 A1 | 6/2003 | Subramanian et al. |
| 2004/0232049 A1 | 11/2004 | Dath et al. |
| 2006/0019360 A1 | 1/2006 | Verser et al. |
| 2006/0102520 A1 | 5/2006 | Lapinski et al. |
| 2006/0127999 A1 | 6/2006 | Verser et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0281354 A1 | 11/2009 | Mariansky et al. |
| 2009/0318573 A1 | 12/2009 | Stites et al. |
| 2010/0016454 A1 | 1/2010 | Gracey et al. |
| 2010/0029995 A1 | 2/2010 | Johnston et al. |
| 2010/0029996 A1 | 2/2010 | Danjo et al. |
| 2010/0121114 A1 | 5/2010 | Johnston et al. |
| 2010/0137630 A1 | 6/2010 | Garton et al. |
| 2010/0145097 A1 | 6/2010 | Brtko et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197486 A1 | 8/2010 | Johnston et al. |
| 2010/0197985 A1 | 8/2010 | Johnston et al. |
| 2010/0249479 A1 | 9/2010 | Berg-Slot et al. |
| 2010/0273229 A1 | 10/2010 | Verser et al. |
| 2010/0311138 A1 | 12/2010 | Padgett |
| 2011/0004033 A1* | 1/2011 | Johnston et al. ............... 568/885 |
| 2011/0004034 A1 | 1/2011 | Daniel et al. |
| 2011/0060169 A1 | 3/2011 | Kaizik et al. |
| 2011/0082322 A1 | 4/2011 | Jevtic et al. |
| 2011/0098501 A1 | 4/2011 | Johnston et al. |
| 2011/0190547 A1 | 8/2011 | Jevtic et al. |
| 2011/0190548 A1 | 8/2011 | Jevtic et al. |

FOREIGN PATENT DOCUMENTS

| | | |
|---|---|---|
| CN | 102228831 | 11/2011 |
| EP | 0104197 | 4/1984 |
| EP | 0167300 | 1/1986 |
| EP | 0175558 | 3/1986 |
| EP | 0 192 587 | 8/1986 |
| EP | 0198682 | 10/1986 |
| EP | 0285420 | 10/1988 |
| EP | 0 400 904 | 5/1990 |
| EP | 0 372 847 | 6/1990 |
| EP | 0 408 528 | 7/1990 |
| EP | 0 653 242 | 5/1995 |
| EP | 1262234 | 12/2002 |
| EP | 1277826 | 1/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 1168785 | 10/1969 |
| GB | 1559540 | 1/1980 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 83/03409 | 10/1983 |
| WO | WO 2005/102513 | 11/2005 |
| WO | WO 2009/009320 | 1/2009 |
| WO | WO 2009/009322 | 1/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/105860 | 9/2009 |

(56) References Cited

FOREIGN PATENT DOCUMENTS

| WO | WO 2010/014151 | 2/2010 |
|---|---|---|
| WO | WO 2010/014153 | 2/2010 |
| WO | WO 2010/055285 | 5/2010 |
| WO | WO 2011/053365 | 5/2011 |

OTHER PUBLICATIONS

Ordéñz et al., The role of metal and support sites on the hydrogenation of acetic acid on Ru-based catalysts, 21st NAM San Francisco, CA, Jun. 10, 2009.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

T. Yokoyama, et al., "Carboxylic Acids and Derivatives", Fine Chemicals through Heterogenous Catalysis, pp. 370-379, (2001).

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., Reactions of Carboxylic Acids on Oxides, Journal of Catalysis 168: 255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Claus, et al., "Selective Hydrogenolysis of Methyl and Ethyl Acetate in the Gas Phase on Copper and Supported Group VIII Metal Catalysts", Applied Catalysis A, 79, 1991, pp. 1-18.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2009/004197 mailed Mar. 24, 2010.

International Search Report and Written Opinion for PCT/US2009/004195 mailed Mar. 26, 2010.

\* cited by examiner

CHEMISORPTION OF ETHYL ACETATE DURING HYDROGENATION OF ACETIC ACID TO ETHANOL

FIELD OF THE INVENTION

The present invention relates to a catalyst that chemisorbs ethyl acetate at the reaction temperature for hydrogenating acetic acid and/or ethyl acetate to ethanol. A catalyst that adsorbs ethyl acetate with suitable strength is useful for producing ethanol without net production of ethyl acetate when a mixed stream of acetic acid and ethyl acetate is used as a feedstock.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; and/or (iv) insufficient catalyst life.

SUMMARY OF THE INVENTION

In a first embodiment, the present invention is directed to a hydrogenation catalyst for converting a mixture comprising acetic acid and ethyl acetate to ethanol at a first temperature, the catalyst comprising one or more active metals or oxide thereof on a support that comprises tungsten or an oxide thereof, wherein the one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum, and wherein the catalyst desorbs ethyl acetate, in the absence of hydrogen, at a second temperature that is greater than the first temperature. The catalyst has a chemisorption of ethyl acetate at the first temperature in the absence of hydrogen. In one embodiment, the first temperature ranges from 125° C. to 350° C. and the second temperature ranges from 300° C. to 600° C.

In a second embodiment, the present invention is directed to a hydrogenation catalyst for converting a mixture comprising acetic acid and ethyl acetate to ethanol at a first temperature, the catalyst comprising a first metal or oxide thereof, a second metal or oxide thereof, and a third metal or oxide thereof, on a support, provided that the first metal is reduced after hydrogen treatment and the second and third metals are partly reduced after hydrogen treatment, wherein the hydrogen treated catalyst has an ethyl acetate desorption peak at a second temperature that is greater than an ethyl acetate desorption peak at the first temperature.

The first metal or oxide thereof may be selected from the group consisting of rhodium, rhenium, ruthenium, platinum, palladium, osmium, iridium and gold. The second metal or oxide thereof may be selected from the group consisting of copper, iron, cobalt, nickel, zinc, and molybdenum. The third metal or oxide thereof may be selected from the group consisting of copper, molybdenum, tin, chromium, iron, cobalt, vanadium, palladium, platinum, lanthanum, cerium, manganese, ruthenium, rhenium, gold, and nickel. The third metal and the second metal are different than the first metal.

In a third embodiment, the present invention is directed to a hydrogenation catalyst for converting a mixture comprising acetic acid and ethyl acetate to ethanol at a first temperature, the catalyst comprising one or more active metals on a support, wherein the catalyst has an ethyl acetate adsorption capacity (Type III+IV) that is from 30 to 70 $\mu mol/g_{cat}$ at a second temperature that is greater than the first temperature. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum.

In a fourth embodiment, the present invention is directed to a process for producing ethanol comprising contacting a feed stream comprising acetic acid, ethyl acetate, and hydrogen at a reactor temperature from 125° C. to 350° C. with a hydrogenating catalyst comprising one or more active metals or oxide thereof on a support to form ethanol wherein the support comprises tungsten or an oxide thereof. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum. The catalyst desorbs ethyl acetate, in the absence of hydrogen, at a second temperature that is greater than the reactor temperature.

In a fifth embodiment, the present invention is directed to a process for producing ethanol comprising contacting a feed stream containing acetic acid, ethyl acetate, and hydrogen at a reactor temperature with a hydrogenating catalyst comprising a first metal or oxide thereof, a second metal or oxide thereof, and a third metal or oxide thereof, on a support, provided that the first metal is reduced after hydrogen treatment and the second and third metals are partly reduced after hydrogen treatment, wherein the hydrogen treated catalyst has an ethyl acetate desorption peak to a second temperature greater than the first temperature.

In a sixth embodiment, the present invention is directed to a process for producing ethanol comprising: passing a gaseous mixture comprising acetic acid, ethyl acetate, and hydrogen over a catalyst at a first temperature, the catalyst comprising one or more active metals on a support, wherein the one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum; and wherein the catalyst has an ethyl acetate adsorption capacity (Type III+IV) that is from 30 to 70 $\mu mol/g_{cat}$ at a second temperature that is greater than the first temperature.

In a seventh embodiment, the present invention is directed to a process for producing ethanol comprising: passing a gaseous mixture comprising acetic acid, ethyl acetate, and hydrogen over a catalyst at a first temperature, wherein ethyl acetate is chemisorbed on the catalyst at the first temperature in the absence of hydrogen, and ethyl acetate is desorbed from the catalyst at a second temperature that is greater than the first temperature.

In an eighth embodiment, the present invention is directed to a process for producing ethanol comprising: passing a gaseous mixture acetic acid, ethyl acetate, and hydrogen over a hydrogen treated catalyst having at least one reduced metal at a first temperature, wherein the hydrogen treated catalyst has an ethyl acetate desorption peak at a second temperature that is greater than an ethyl acetate desorption peak at the first temperature.

In a ninth embodiment, the present invention is directed to a process for producing ethanol comprising: passing a gaseous mixture comprising acetic acid, ethyl acetate, and hydrogen over a catalyst at a first temperature, wherein the catalyst has an ethyl acetate adsorption capacity (Type III+IV) that is from 30 to 70 $\mu mol/g_{cat}$ at a second temperature that is greater than the first temperature.

BRIEF DESCRIPTION OF THE DRAWINGS

The present invention will be better understood in view of the appended non-limiting figures, in which.

DETAILED DESCRIPTION OF THE INVENTION

Figure 1:
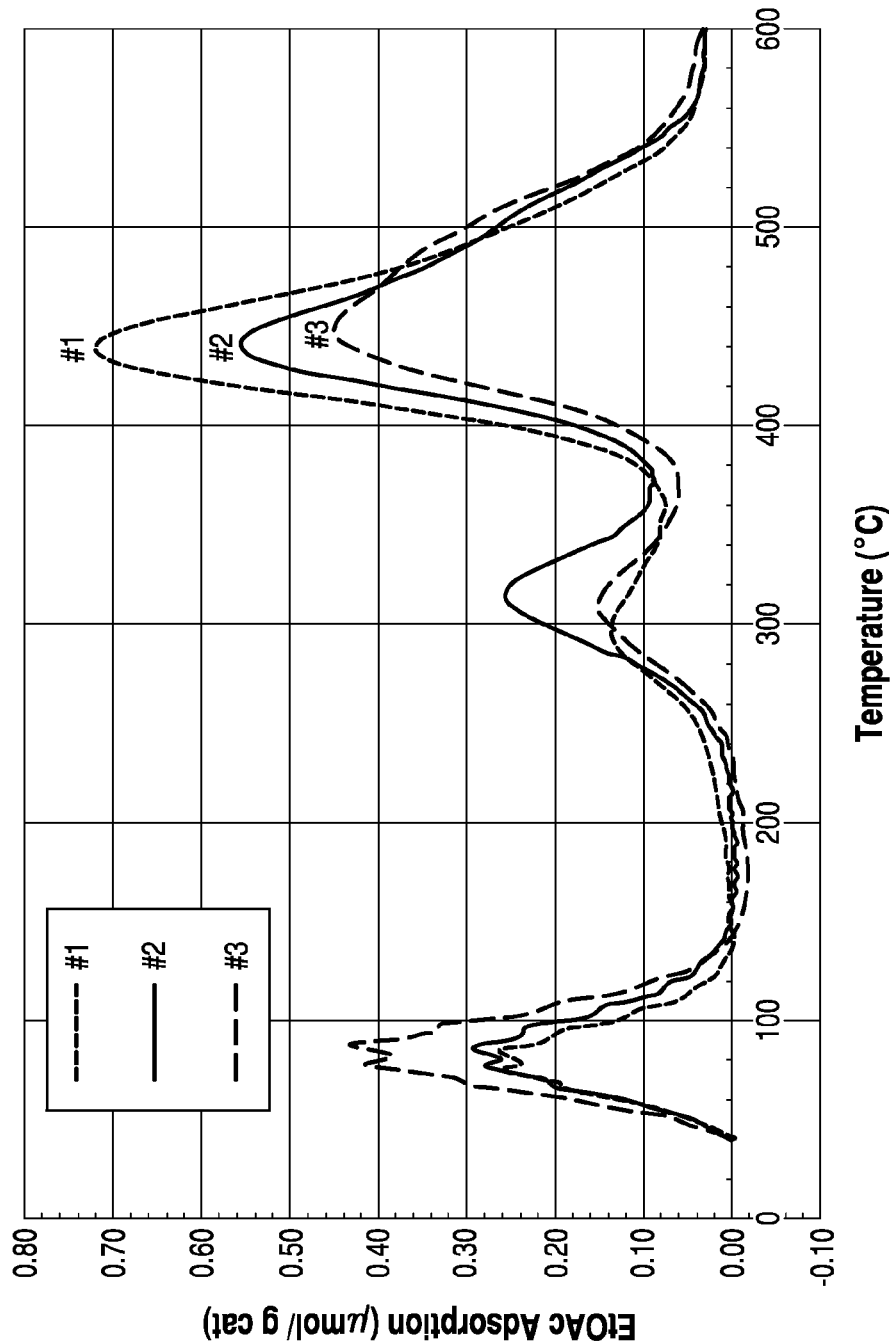
FIG. 1 is a temperature programmed desorption profile for catalysts according to one exemplary embodiment of the present invention.

The present invention is directed to catalyst compositions for converting a mixture of acetic acid and ethyl acetate to ethanol. In one embodiment, the catalysts of the present invention have chemisorptions of ethyl acetate, in the absence of hydrogen, at the reaction temperature for hydrogenating acetic acid to ethanol. Without being bound by theory, this allows ethyl acetate to be adsorbed on the catalyst surface and may convert ethyl acetate to ethanol. Ethyl acetate may evolve at a temperature that is greater than the reaction temperature. Ethyl acetate production may be avoided or reduced when the catalyst evolves or desorbs ethyl acetate at a temperature that is greater than the reaction temperature. In one embodiment, the reaction temperature or first temperature, may be from 125° C. to 350° C., e.g., from 200° C. to 325° C., from 225° C. to 300° C., or from 250° C. to 300° C. In one embodiment, the evolution or desorption of temperature of ethyl acetate at second temperature, in the absence of hydrogen, may be from 300° C. to 600° C., e.g., from 320° C. to 500° C. or from 340° C. to 450° C. Preferably, the second temperature, in the absence of hydrogen, is greater than the first temperature, in the presence of hydrogen. It is understood that because no hydrogen is present at the second temperature that the hydrogenation reactor is preferably carried out at the first temperature and generally not the second temperature. Without being bound by theory, with higher desorption temperatures than reaction temperatures, ethyl acetate molecules will stay on the adsorption site until those molecules reacts with hydrogen to form ethanol. A catalyst is more likely to hydrogenate ethyl acetate to ethanol when ethyl acetate is adsorbed on the catalyst at the reaction temperature for converting acetic acid to ethanol.

In one embodiment, under steady state conditions, the catalysts are not a net producer of ethyl acetate and thus the conversion of ethyl acetate is 0% or greater. Preferably, ethyl acetate is converted to ethanol. During the hydrogenation of acetic acid, there may be a side esterification reaction of the acetic acid and ethanol to form ethyl acetate. The catalysts that are capable of chemisorbing ethyl acetate at the hydrogenation temperature of acetic acid have been found to have a reaction rate of ethyl acetate that substantially equates to the formation of ethyl acetate. Under steady state conditions, ethyl acetate that is formed is recycled back to the reactor to reduce the purging and increase ethanol recovery. Because ethyl acetate is recycled to the reactor, it is necessary for the catalyst of the present invention to have a conversion of ethyl acetate that is 0% or greater under steady state conditions. In evaluating no net production of ethyl acetate, i.e. 0% conversion, the level of ethyl acetate in the recycle loops to the reactor is compared to the amount of ethyl acetate out of the reactor at steady state conditions. Fresh acetic acid and ethyl acetate from the recycle loop will make up the liquid feed to reactor. The weight percentage of ethyl acetate in the recycle loop may vary depending on the ability of the catalysts to convert ethyl acetate to avoid production of ethyl acetate. In one exemplary embodiment, the liquid feed comprises from 0.1 to 50 wt. % ethyl acetate, e.g., from 0.5 to 20 wt. % or from 1 to 10 wt. % Higher catalyst activity may decrease the concentration of ethyl acetate.

On a per pass basis, the conversion of ethyl acetate may be higher, and is preferably greater than 5%, greater than 15% or greater than 35%. A negative conversion or a net production of ethyl acetate would result in an undesirable buildup of ethyl acetate. The present invention advantageously allows the process to continuously recycle ethyl acetate without causing a buildup in the system.

The catalysts preferably comprise one or more active metals or oxide thereof on a support, preferably a modified support, and may be suitable in catalyzing the hydrogenation of a carboxylic acid, e.g., acetic acid, and/or esters thereof, e.g., ethyl acetate, to the corresponding alcohol, e.g., ethanol. In one preferred embodiment, the support comprises tungsten or an oxide thereof. Tungsten or an oxide thereof may be a support modifier that adjusts the acidity of the support. In other embodiments, the support may comprise tungsten, molybdenum, vanadium, niobium, tantalum, and oxides thereof, or mixtures thereof.

In one embodiment the catalysts are capable of converting both carboxylic acids, such as acetic acid, and esters thereof, e.g., ethyl acetate, to their corresponding alcohol(s), e.g., ethanol, under hydrogenation conditions. More preferably, the catalyst may have an acetic acid conversion greater than 20%, greater than 75% or greater than 90% under steady state conditions, and an ethyl acetate conversion, under one pass, of greater than 5%, greater than 15% or greater than 35%. The ethyl acetate conversion under steady state conditions is 0% or greater.

The catalysts of the invention preferably include one or more active metals or oxide thereof. The one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum. The total metal loading of the one or more active metals is from 0.1 to 25 wt. %, e.g., from 0.5 to 20 wt. % or from 0.6 to 15 wt. %. In one embodiment, the one or more active metals may include a precious metal that is selected from the group consisting of rhodium, rhenium, ruthenium, platinum, palladium, osmium, iridium and gold. The precious metal may be in elemental form or in molecular form, e.g., an oxide of the precious metal. It is preferred that the catalyst comprises such precious metals in an amount less than 5 wt. %, e.g., less than 3 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst.

In another embodiment, the catalyst may comprise two active metals or three active metals. The first metal or oxide thereof may be selected from the group consisting of cobalt, rhodium, rhenium, ruthenium, platinum, palladium, osmium, iridium and gold. The second metal or oxide thereof may be selected from the group consisting of copper, iron, tin, cobalt, nickel, zinc, and molybdenum. The third metal or oxide thereof, if present, may be selected from the group consisting of copper, molybdenum, tin, chromium, iron, cobalt, vanadium, palladium, platinum, lanthanum, cerium, manganese, ruthenium, rhenium, gold, and nickel. Preferably, the third metal is different than the first metal and the second metal. In addition, the first metal and the second metal may be different, and the third metal and the second metal may be different.

The metal loadings of the first, second, and optionally third metals are as follows. The first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 5 wt. %. If the catalyst further comprises a third active metal, the third active metal may be present in an amount from 0.05 to 20 wt. %, from 0.05 to 10 wt. %, or from 0.05 to 5 wt. %. The active metals may be alloyed with one another or may comprise a non-alloyed metal solution, a metal mixture or be present as one or more metal oxides. For purposes of the present specification, unless otherwise indicated, weight percent is based on the total weight the catalyst including metal and support.

Bimetallic catalysts for some exemplary catalyst compositions include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel, cobalt/tin, and rhodium/tin. More preferred bimetallic catalysts include platinum/tin, platinum/cobalt, platinum/nickel, palladium/cobalt, palladium/copper, palladium/nickel, ruthenium/cobalt, ruthenium/iron, rhodium/iron, rhodium/cobalt, rhodium/nickel, cobalt/tin, and rhodium/tin.

In some embodiments, the catalyst may be a ternary catalyst that comprises three active metals on a support. Exemplary tertiary catalysts may include palladium/tin/rhenium, palladium/cobalt/rhenium, palladium/nickel/rhenium, palladium/cobalt/tin, platinum/tin/palladium, platinum/tin/rhodium, platinum/tin/gold, platinum/tin/iridium, platinum/cobalt/tin, platinum/tin/chromium, platinum/tin/copper, platinum/tin/zinc, platinum/tin/nickel, rhodium/nickel/tin, rhodium/cobalt/tin and rhodium/iron/tin. More preferably, a ternary catalyst comprises three active metals may include palladium/cobalt/tin, platinum/tin/palladium, platinum/cobalt/tin, platinum/tin/chromium, platinum/tin/copper, platinum/tin/nickel, rhodium/nickel/tin, rhodium/cobalt/tin and rhodium/iron/tin. In one exemplary embodiment, a catalyst that comprises platinum/cobalt/tin may have a chemisorption of ethyl acetate at the hydrogenation reaction temperature of acetic acid.

In one embodiment, the ternary combination comprises cobalt and/or tin and at least one other active metal. In one embodiment, the first and second active metals are present as cobalt and tin, and are present at a cobalt to tin molar ratio from 6:1 to 1:6 or from 3:1 to 1:3. In another embodiment, the cobalt and tin are present in substantially equimolar amounts, that is, in a molar ratio from 1.2:1 to 1:1.2 and more preferably a molar ratio of 1:1.

In one embodiment, the first metal is reduced after hydrogen treatment and the second and third metals, if present, are partly reduced after conditioning, e.g. hydrogen treatment. In some embodiments, the second and/or third metals may also be reduced after hydrogen treatment. Hydrogen treatment involves exposing the catalyst to hydrogen prior to the organic reactants, preferably at a temperature of 225° C. to 375° C., e.g., from 225° C. to 350° C. or from 250° C. to 300° C. In addition, the first metal may be reduced for a used catalyst. A used catalyst refers to a catalyst in which a flow of organic reactants has been passed over the catalyst for a period of time or the time on stream (TOS). Typically used catalysts have at least 5 hours TOS, e.g., at least 10 hours TOS or at least 50 hours TOS. In some embodiments, the second and/or third metals for a used catalyst may be reduced or partially reduced.

When at least one of the active metals are reduced, the hydrogen treated catalyst or used catalyst may have an ethyl acetate desorption peak at a second temperature that is greater than the ethyl acetate desorption peak at the first temperature, i.e. the hydrogenation temperature for reducing acetic acid to ethanol. Different types of adsorption sites are formed after reduction when observing the desorption temperature shift.

The magnitude of the peak may also indicate the capability of the catalyst to adsorb or desorb ethyl acetate. A weak peak may indicate that the catalyst does not readily adsorb ethyl acetate. Thus, there may be a reduction in the hydrogenation of ethyl acetate to ethanol and a weak peak may result in a higher concentration of ethyl acetate in the crude ethanol product. Also this may lead to negative conversions. Larger peaks are more preferred for the present invention because the larger peak indicates that ethyl acetate can readily adsorb on the surface, but desorbs at the designated higher second temperature. Desorption of ethyl acetate is preferably at a maximum at the second temperature.

In one exemplary embodiment, the adsorption capacity (Type II) at the first temperature and adsorption capacity (Type III and Type IV) at the second temperature may be determined by a temperature programmed desorption (TPD) at ambient pressure. Adsorption capacity may increase as pressure of TPD increases. The units may be normalized based on the grams of catalyst. Adsorption capacity (Type II) at the first temperature may range from 5 to 30 $\mu mol/g_{cat}$, e.g. from 10 to 25 $\mu mol/g_{cat}$, or from 10 to 20 $\mu mol/g_{cat}$. Adsorption capacity (Type III+IV) at the second temperature may range from 30 to 70 $\mu mol/g_{cat}$, e.g. from 40 to 60 $\mu mol/g_{cat}$, or from 40 to 55 $\mu mol/g_{cat}$.

A fresh catalyst, one that has not been exposed to hydrogen, acetic acid and/or ethyl acetate, may not be well activated. Thus, it is preferred to determine the ethyl acetate chemisorption of a used catalyst to represent a catalyst under expected operational conditions in an industrial process.

The catalysts of the present invention comprise a suitable support material, preferably a modified support material. In one embodiment, the support material may be an inorganic oxide. In one embodiment, the support material may be selected from the group consisting of silica, alumina, titania, silica/alumina, pyrogenic silica, high purity silica, zirconia, carbon (e.g., carbon black or activated carbon), zeolites and mixtures thereof. Zeolites may include high silica zeolites (HSZ™ Tosoh Products) that contain more silica than alumina. Silica gel may be used as a precursor for preparing silica containing supports. Preferably, the support material comprises silica. In preferred embodiments, the support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a silicaceous support material, e.g., silica, having a surface area of at least 50 $m^2/g$, e.g., at least 100 $m^2/g$, at least 150 $m^2/g$, at least 200 $m^2/g$ or at least 250 $m^2/g$. In terms of ranges, the silicaceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 250 $m^2/g$. For purposes of the present specification, surface area refers to BET nitrogen surface area, meaning the surface area as determined by ASTM D6556-04, the entirety of which is incorporated herein by reference.

The preferred silicaceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

The support material preferably comprises a support modifier. A support modifier may adjust the acidity of the support material. As stated above, in one preferred embodiment, the support comprises tungsten or an oxide thereof that is a support modifier. In other embodiments, the support may comprise tungsten, molybdenum, vanadium, niobium, tantalum, and oxides thereof, or mixtures thereof. In one embodiment, tungsten, molybdenum, vanadium, niobium, tantalum, and oxides thereof, or mixtures thereof may be in an amount from 4 to 30 wt. %, e.g., from 8 to 35 wt. % or from 12 to 20 wt. %.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production. In addition, the support modifier may have a low volatility or no volatility.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. Acidic support modifiers include those selected from the group consisting of $WO_3$, $TiO_2$, $ZrO_2$, $Nb_2O_5$, $Ta_2O_5$, $Al_2O_3$, $B_2O_3$, $P_2O_5$, $Sb_2O_3$, $MoO_3$, $Fe_2O_3$, $Cr_2O_3$, $V_2O_5$, $MnO_2$, $CuO$, $Co_2O_3$, $Co_3O_4$, and $Bi_2O_3$. Preferred acidic support modifiers include those selected from the group consisting of $TiO_2$, $ZrO_2$, $Nb_2O_5$, $Ta_2O_5$, $WO_3$, $MoO_3$, and $Al_2O_3$. The acidic modifier may also include those selected from the group consisting of $WO_3$, $MoO_3$, $V_2O_5$, $VO_2$, $V_2O_3$, $Nb_2O_5$, $Ta_2O_5$, $FeO$, $Fe_3O_4$, $Fe_2O_3$, $Cr_2O_3$, $MnO_2$, $CoO$, $Co_2O_3$, and $Bi_2O_3$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $Mo_9O_{26}$, $Mo_8O_{23}$, $Mo_5O_{14}$, $Mo_{17}O_{47}$, $Mo_4O_{11}$, or $MoO_2$.

In one embodiment, the support modifiers are present in an amount from 0.1 wt. % to 50 wt. %, e.g., from 0.2 wt. % to 25 wt. %, from 0.5 wt. % to 15 wt. %, or from 1 wt. % to 12 wt. %, based on the total weight of the catalyst.

In some embodiments, the acidic support modifier comprises an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and manganese tantalate. Polyoxometalates (POMs) and their corresponding heteropoly acids (HPAs) may also be used as the precursors for the support modifier.

In one embodiment, the catalyst comprises from 0.25 to 1.25 wt. % platinum, from 1 to 10 wt. % cobalt, and from 1 to 10 wt. % tin on a silica or a silica-alumina support material. The support material may comprise from 5 to 15 wt. % acidic support modifiers, such as $WO_3$, $V_2O_5$ and/or $MoO_3$.

The present invention also relates to processes for making the catalyst. Without being bound by theory, the process for making the catalyst may improve one or more of acetic acid conversion, ester conversion, ethanol selectivity and overall productivity. In one embodiment, the support is modified with one or more support modifiers and the resulting modified support is subsequently impregnated with one or more active metals to form the catalyst composition. For example, the support may be impregnated with a support modifier solution comprising a support modifier precursor. After drying and calcination, the resulting modified support is impregnated with a second solution comprising one or more of the active metal precursors, followed by drying and calcination to form the final catalyst.

In some embodiments, the support modifier may be added as particles to the support material. For example, one or more support modifier precursors, if desired, may be added to the support material by mixing the support modifier particles with the support material, preferably in water. When mixed it is preferred for some support modifiers to use a powdered material of the support modifiers. If a powdered material is employed, the support modifier may be pelletized, crushed and sieved prior to being added to the support.

Impregnation of the one or more active metals onto the support, e.g., modified support, may occur simultaneously (co-impregnation) or sequentially. In simultaneous impregnation, the two or more metal precursors are mixed together and added to the support, preferably modified support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal precursors in the event the two precursors are incompatible with the desired solvent, e.g., water.

In sequential impregnation, the first metal precursor may be first added to the support followed by drying and calcining, and the resulting material may then be impregnated with the second metal precursor followed by an additional drying and calcining step to form the final catalyst composition. Additional metal precursors (e.g., a third metal precursor) may be added either with the first and/or second metal precursor or in a separate third impregnation step, followed by drying and calcination. Of course, combinations of sequential and simultaneous impregnation may be employed if desired.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, a support modifier precursor, and preferably one or more active metal precursors. The solution is stirred and combined with the support material using, for example, incipient wetness impregnation in which the support modifier precursor is added to a support material having the same pore volume as the volume of the solution. Impregnation occurs by adding, optionally drop wise, a solution containing the precursors of either or both the support modifiers and/or active metals, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 100° C. to 200° C. or about 120° C., optionally for a period from 1 to 24 hours, e.g., from 3 to 15 hours or from 6 to 12 hours. The dried support may be calcined optionally with ramped heating, for example, at a temperature from 300° C. to 900° C., e.g., from 400° C. to 750° C., from 500° C. to 600° C. or at about 550° C., optionally for a period of time from 1 to 12 hours, e.g., from 2 to 10 hours, from 4 to 8 hours or about 6 hours, to form the final modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified support and, ultimately, the final catalyst.

Use of Catalyst to Hydrogenate Acetic Acid and Ethyl Acetate

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid and ethyl acetate, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment the invention is a process for producing ethanol by hydrogenating a feedstock comprising compounds selected from acetic acid, ethyl acetate and mixtures thereof in the presence of any of the above-described catalysts. The catalyst may be characterized as a "bifunctional" catalyst in that it effectively catalyzes the hydrogenation of acetic acid to ethanol as well as the conversion of ethyl acetate to one or more products, preferably ethanol. As stated above, even through the catalyst may convert ethyl acetate, the net conversion under steady state condition is 0% or greater.

In one embodiment, the feed stream is a mixed feed comprising both acetic acid and ethyl acetate. Ethyl acetate may be recycled under steady state. Preferably, the mixed feed comprises from 5 to 40 wt. % ethyl acetate and from 60 to 95 wt. % acetic acid, and more preferably from 10 to 30 wt. % ethyl acetate and 70 to 90 wt. % acetic acid. In one embodiment, the mixed feed comprises 30 wt. % ethyl acetate and 70 wt. % acetic acid. In another embodiment, the mixed feed comprises 15 wt. % ethyl acetate and 85 wt. % acetic acid. In still another embodiment, the mixed feed comprises 10 wt. % ethyl acetate and 90 wt. % acetic acid.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid and/or ethyl acetate may be vaporized at the reaction temperature, following which the vaporized acetic acid and/or ethyl acetate may be fed along with hydrogen in an undiluted state or diluted with a relatively inert carrier gas, such as nitrogen, argon, helium, carbon dioxide or the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 150° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of a carboxylic acid, e.g., acetic acid, to its corresponding alcohol, e.g., ethanol, and a second bifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2500 kPa, or from 100 kPa to 2250 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1. For a mixed feedstock, the molar ratio of hydrogen to ethyl acetate may be greater than 5:1, e.g., greater than 10:1 or greater than 15:1.

Contact or residence time can also vary widely, depending upon such variables as amount of feedstock (acetic acid and/or ethyl acetate), catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, by employing the catalysts of the invention, the hydrogenation of acetic acid and/or ethyl acetate may achieve favorable conversion and favorable selectivity and productivity to ethanol in the reactor. For the purposes of the present invention, the term "conversion" refers to the net change of the flow of acetic acid or ethyl acetate into the reactor as compared to the flow of acetic acid or ethyl acetate out of the reactor. Conversion is expressed as a percentage based on acetic acid or ethyl acetate in the feed. The acetic acid conversion may be at least 20%, more preferably at least 60%, at least 75%, at least 80%, at least 90%, at least 95% or at least 99%.

During the hydrogenation of acetic acid, ethyl acetate may be produced as a byproduct. Without consuming any ethyl acetate, the conversion of ethyl acetate would be deemed negative. The use of monofunctional catalysts, i.e. a catalyst that converts one of the reactants, may result in the undesirable build up of ethyl acetate in the system, particularly for systems employing one or more recycle streams to the reactor.

The preferred catalysts of the invention, however, are bifunctional in that they effectively catalyze the conversion of acetic acid to ethanol as well as the conversion of an alkyl acetate such as ethyl acetate to one or more products other than that alkyl acetate. The bifunctional catalyst is preferably effective for consuming ethyl acetate at a rate sufficiently great so as to at least offset the rate of ethyl acetate production, thereby resulting in a non-negative ethyl acetate conversion, i.e., no net increase in ethyl acetate is realized. The use of such catalysts may result, for example, in an ethyl acetate conversion that is effectively 0% or that is 0% or greater at steady state conditions. After the process reaches steady state the amount of ethyl acetate formed will substantially equal the amount of ethyl acetate recycled. Catalysts having a higher ethyl acetate conversion may preferably result in a lower concentration of ethyl acetate in the recycle loop and thus lower ethyl acetate in the mixed feed. On a per pass, the catalysts of the invention are effective in providing ethyl acetate conversions of at least 5%, e.g., at least 10%, at least 15%, at least 20%, or at least 35%.

In continuous processes, ethyl acetate being added (e.g., recycled) to the hydrogenation reactor and ethyl acetate leaving the reactor in the crude product preferably approaches a certain level after the process reaches equilibrium. The use of a bifunctional catalyst that catalyzes the conversion of ethyl acetate as well as acetic acid results in a lower amount of ethyl acetate added to the reactor and less ethyl acetate produced relative to monofunctional catalysts. In preferred embodiments, the concentration of ethyl acetate in the mixed feed and crude product is less than 40 wt. %, less than 25 wt. % or less than 15 wt. % after equilibrium has been achieved. In preferred embodiments, the process forms a crude product comprising ethanol and ethyl acetate, and the crude product has an ethyl acetate steady state concentration from 0.1 to 40 wt %, e.g., from 0.1 to 20 wt % or from 0.1 to 15 wt %.

Although catalysts that have high acetic acid conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid and/or ethyl acetate. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the combined converted acetic acid and ethyl acetate. Preferably, total selectivity to ethanol is at least 60%, e.g., at least 70%, or at least 80%, at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 35 | 10 to 32 | 10 to 30 |
| Ethyl Acetate | 0 to 30 | 0 to 25 | 1 to 20 | 3 to 15 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. In some embodiments, when further water separation is used, the ethanol product preferably contains ethanol in an amount that is greater than 96 wt. %, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The following examples describe the catalyst and process of this invention.

EXAMPLES

Surface reactions and molecular adsorption on surfaces can be studied very effectively using Temperature Programmed Desorption (TPD). The TPD technique involves the adsorption of a species on the surface of the catalyst at low temperature, e.g., close to room temperature, and heating the sample at a linear ramp rate while monitoring the species that evolve from the surface of the catalyst. Desorption of the gas from the surface produces a signal in the detector. This signal is plotted against temperature to obtain the TPD profile as shown in FIG. 1. Generally, the area under the peak of the desorbed signal will be proportional to the amount of adsorbed gas. In other words, the area under the curve may be indicative of the surface coverage. The position of peak temperature may be indicative of the strength of adsorption. If there are multiple binding sites on the surface, multiple peak temperatures are observed in the TPD graph.

In some embodiments, TPD experiments may be carried out on catalysts suitable for use with the present invention using ethyl acetate. For example, 40% ethyl acetate vapor in helium gas with a flow at 50 sccm was pulse dosed on about 0.3 grams of conditioned catalyst held at 40° C. until saturation of adsorbed acetic acid was achieved. Catalyst conditioning was achieved by heating the catalyst, e.g., to 350° C. for 2 hours, to remove moisture and any surface contaminants. The catalyst was then cooled, e.g., to 40° C., and pulse adsorption of acetic acid was done. Helium gas at 50 sccm was then passed over the catalyst to remove any loosely held acetic acid. The catalyst was then heated at a linear rate, e.g., 5° C./min from 40 to 600° C., and held at that temperature, e.g., for 1 hour. Desorption of acetic acid was monitored using a thermal conductivity detector (TCD).

The catalysts contained similar active metals and loadings, but the amount of support modifier, namely $WO_3$, varied. The catalyst tested are as follows: A) Pt(1 wt. %)-Co(4.8 wt. %)-Sn(4.1 wt. %) on $SiO_2$—$WO_3$ (8 wt. %); B) Pt(1 wt. %)-Co(4.8 wt. %)-Sn(4.1 wt. %) on $SiO_2$—$WO_3$(12 wt. %); and C) Pt(1 wt. %)-Co(4.8 wt. %)-Sn(4.1 wt. %) on $SiO_2$—$WO_3$ (16 wt. %).

For each catalyst, the adsorption capacity (Type II) is shown as a peak between 125° C. to 350° C. Adsorption capacity (Type III+IV) is shown as a peak between above 350° C. Table 2 reports the adsorption capacities. The values were normalized for 1 gram of catalyst. In addition, after passing a mixed feed of acetic acid and ethyl acetate through the bed containing the catalyst the conversion and selectivity is also shown in Table 2. The composition of the crude ethanol product, as determined by GC, is also provided in Table 2.

TABLE 2

| Catalyst | Adsorption Capacity ($\mu$mol/$g_{cat}$) | | Conversion | | EtOH | GC Products (wt. %) | | |
|---|---|---|---|---|---|---|---|---|
| | Type II | Type III + IV | HOAc | EtOAc | Sel. % | EtOH | EtOAc | DEE |
| A | 11.5 | 43.7 | 98.2 | 15.7 | 94.96 | 58.1 | 17.2 | 0.06 |
| B | 16.9 | 47.6 | 99.4 | 23.9 | 94.31 | 60.6 | 15.7 | 0.12 |
| C | 11.5 | 55.02 | 99.7 | 36.9 | 96.12 | 63.8 | 12.9 | 0.25 |

Figure 2:
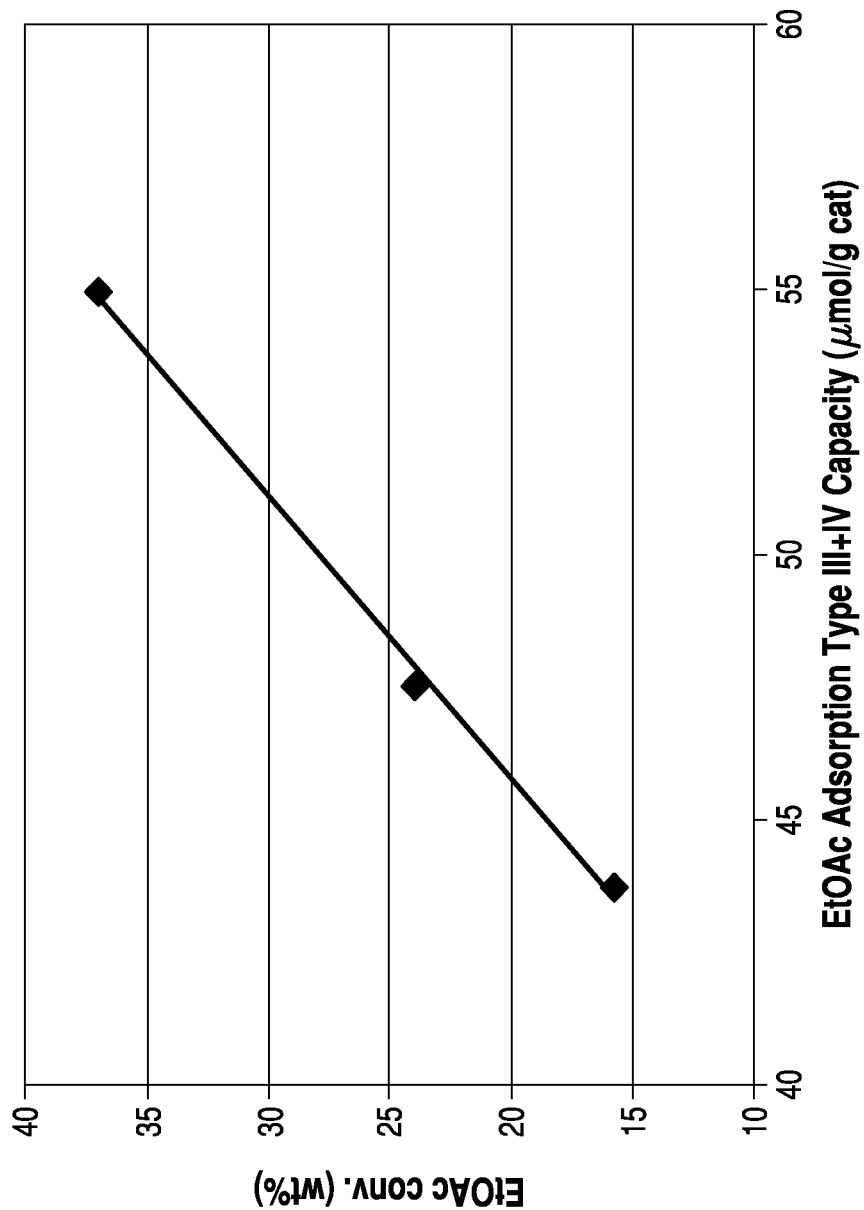
FIG. 2 is a graph of ethyl acetate conversion and adsorption capacities (Type III+Type IV) according to one exemplary embodiment of the present invention.

FIG. 2 is a graph showing the correlation of the adsorption capacity (Type III+IV) with ethyl acetate conversion after one pass.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

What is claimed is:

1. A process for producing ethanol comprising: contacting a feed stream comprising acetic acid, ethyl acetate, and hydrogen at a reactor temperature from 125° C. to 350° C. with a hydrogenating catalyst comprising one or more active metals or oxide thereof on a support to form ethanol,
   wherein the support comprises tungsten or an oxide thereof;
   wherein the one or more active metals are selected from the group consisting of cobalt, copper, gold, iron, nickel, palladium, platinum, iridium, osmium, rhenium, rhodium, ruthenium, tin, zinc, lanthanum, cerium, manganese, chromium, vanadium, and molybdenum; and
   wherein the catalyst desorbs ethyl acetate, in the absence of hydrogen, at a second temperature that is greater than the first temperature.

2. The process of claim 1, wherein the second temperature is from 350° C. to 600° C.

3. The process of claim 1, wherein acetic acid conversion is greater than 90%.

4. The process of claim 1, wherein ethyl acetate conversion 0% or greater.

5. The process of claim 1, wherein total selectivity to ethanol is greater than 90%.

6. The process of claim 1, wherein the hydrogenation is performed in a vapor phase at a pressure of 10 kPa to 3000 kPa, and a hydrogen to acetic acid mole ratio of greater than 2:1 and a hydrogen to ethyl acetate mole ratio of greater than 4:1.

7. The process of claim 1, further comprising gasifying a carbonaceous material to produce the feed stream, wherein the carbonaceous material is selected from the group consisting of oil, coal, natural gas and biomass.

* * * * *